US005969617A

United States Patent [19]
Garthe

[11] Patent Number: 5,969,617
[45] Date of Patent: Oct. 19, 1999

[54] FLAME IONIZATION DETECTOR

[75] Inventor: Christopher Garthe, Düsseldorf, Germany

[73] Assignee: Pierburg AG, Neuss, Germany

[21] Appl. No.: 09/188,940

[22] Filed: Nov. 10, 1998

[30] Foreign Application Priority Data

Dec. 13, 1997 [DE]  Germany ............................ 197 55 555

[51] Int. Cl.⁶ .................................................. G08B 17/12
[52] U.S. Cl. ............................ 340/579; 324/468; 431/73; 431/12; 431/25; 431/78; 436/153; 328/6; 361/253
[58] Field of Search ........................... 340/579; 324/468; 436/153; 431/73, 12, 25, 78; 328/6; 361/253

[56] References Cited

U.S. PATENT DOCUMENTS

| | | | |
|---|---|---|---|
| 3,836,857 | 9/1974 | Ikegami et al. ............................. | 328/6 |
| 3,938,956 | 2/1976 | Dimeff ...................................... | 23/254 |
| 4,107,657 | 8/1978 | Nishigaki et al. ....................... | 340/579 |
| 4,410,854 | 10/1983 | Kroneisen et al. ..................... | 324/468 |
| 5,053,343 | 10/1991 | Vora et al. .............................. | 436/153 |
| 5,073,104 | 12/1991 | Kenlo ........................................ | 431/12 |
| 5,073,753 | 12/1991 | Collings et al. ........................ | 324/468 |
| 5,472,337 | 12/1995 | Guerra ...................................... | 431/78 |

FOREIGN PATENT DOCUMENTS

| | | | |
|---|---|---|---|
| 0723154 | 7/1996 | European Pat. Off. ....... | G01N 30/68 |
| 0763733 | 3/1997 | European Pat. Off. ....... | G01N 30/68 |
| 1451795 | 10/1976 | United Kingdom ........... | G01N 30/68 |
| 2138997 | 10/1984 | United Kingdom ............ | H01J 39/28 |

OTHER PUBLICATIONS

Hauschulz, G. "Emissions–und Immessionsmesstechnik im Verkehrswesen" ("Emission and Imission Measurement Technology in Traffic Systems") *Verlag TUV Rheinland GmbH* (1993), pp. 213–215.

*Primary Examiner*—Jeffery A. Hofsass
*Assistant Examiner*—Tai T. Nguyen
*Attorney, Agent, or Firm*—Ladas & Parry

[57] ABSTRACT

A flame ionization detector having a pair of spaced electrodes to which a DC voltage is applied and a flame produced between the electrodes by burning a gas whose composition is to be determined, thereby ions are produced which form an ion current between the electrodes which is representative of the gas composition to be measured. The flame detector is formed by a base plate having a first channel for inlet of the gas whose composition to be measured, a second channel for inlet of a combustion gas, a third channel connected to the first and second channels for conveying a mixture of the gases to an outlet communicating with a nozzle outlet in a ceramic plate on the base plate which faces an opening in a metal plate spaced at a predetermined distance from the ceramic plate such that the flame burns in the opening in the metal plate. An electrically conductive metal layer is disposed on the ceramic plate around the nozzle outlet therein. A negative pole of the DC voltage supply is connected to the metal plate as one of the electrodes and the positive pole of the DC voltage supply is connected to the electrically conductive metal layer as the other of the pair of electrodes. An output line is connected to the electrically conductive metal layer to provide an output signal.

5 Claims, 1 Drawing Sheet

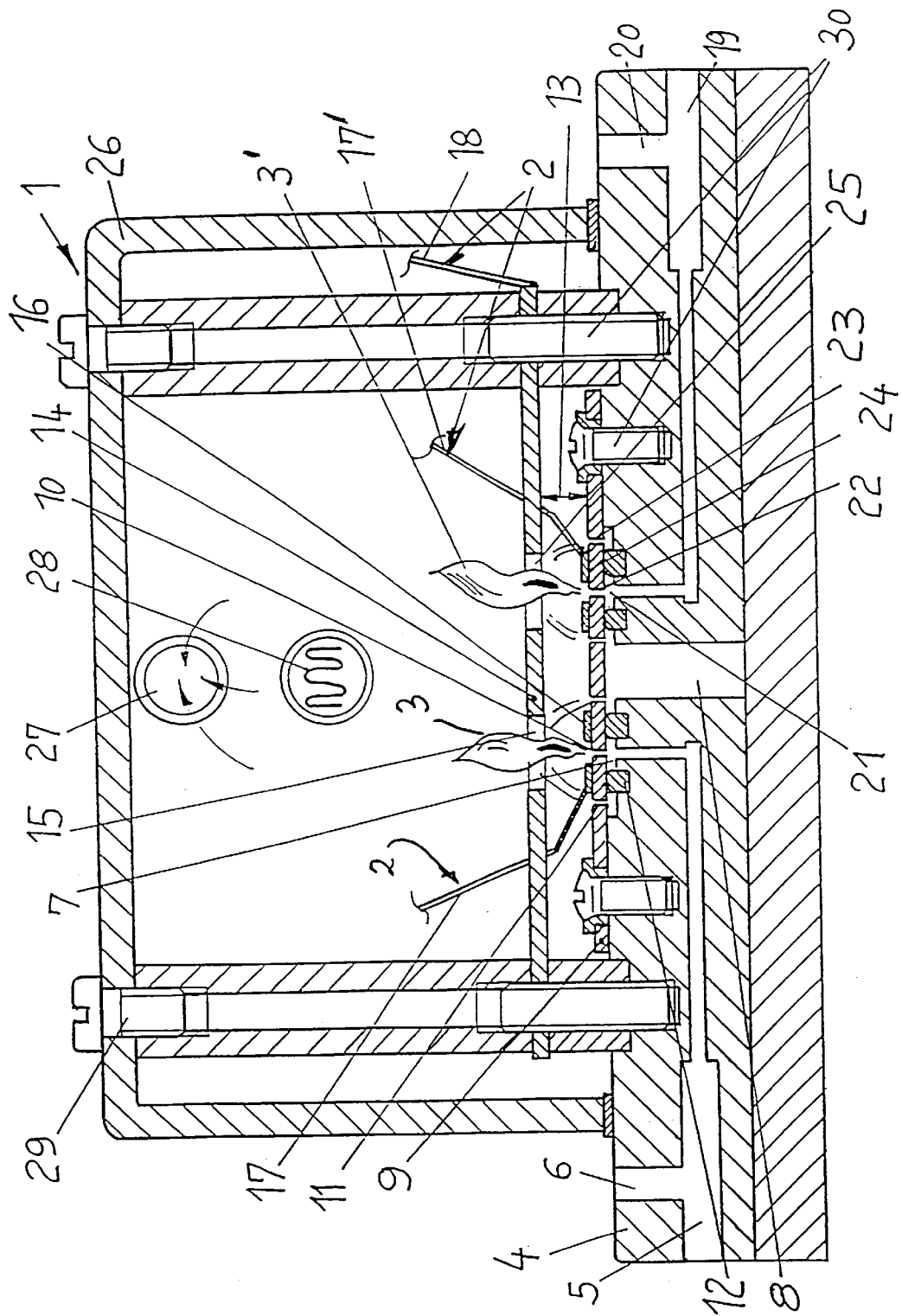

FLAME IONIZATION DETECTOR

FIELD OF THE INVENTION

The invention relates to a flame ionization detector particularly for measuring the content of exhaust gases of an internal combustion engine.

BACKGROUND AND PRIOR ART

Flame ionization detectors have been used for a long time for measuring hydrocarbon concentration in automobile exhaust gases, as described, for example, in publication "Emission and Imission Measurement Technology in Traffic Systems", published by TÜV Rheinland, 1993 printing, page 214.

The measurement principle of the flame ionization detector is based on the fact that ions are formed in a hydrogen flame from hydrocarbon molecules. The flame burns between two electrodes, to which a d.c. voltage is applied. The combustion air and the combustion gas ($H_2$ or an $H_2/He$ mixture) are introduced separately into the burner. The exhaust gas sample is mixed with the combustion gas in front of the burner nozzle. The ions formed by the flame produce a charge, which can be measured as an ion current.

The arrangement of the electrodes with their necessary insulation, screw connections and the like results in a complex mechanical construction which is relatively expensive and leads to high production costs. In addition, this arrangement of the electrodes is not suitable for a design having several channels, for example, for measuring overall hydrocarbon content and specific methane content in the automobile exhaust gas simultaneously.

SUMMARY OF THE INVENTION

It is thus an object of the invention to provide a flame ionization detector of the above type, having lower production costs for its manufacture and a simplified construction in which separate connections for inlet of gases to be measured can be provided, so that several exhaust components can be measured separately. In addition, the structural size of the detector is minimized and involves a minimum assembly cost.

The above and further objects have been achieved by a flame detector comprising a pair of spaced electrodes adapted for supply of a DC voltage thereto and means for producing a flame between the electrodes by burning a gas whose composition is to be determined, said flame producing ions which form an ion current whose measurement is representative of the composition of the gas. The aforesaid means comprises a base plate having a first channel for inlet of the gas to be measured, a second channel for inlet of a combustion gas, a third channel connected to said first and second channels for conveying a mixture of the gases, an outlet for said third channel, and a further channel for inlet of combustion air and further outlets for said combustion air surrounding the outlet for the gas mixture, a ceramic plate on said base plate having a nozzle outlet communicating with said outlet of said third channel for discharging the mixture of the gases therefrom, and further nozzle outlets communicating with said further outlets of said further channel for discharging the combustion air therefrom, a metal plate spaced at a predetermined distance from said ceramic plate, said metal plate having an opening facing said nozzle outlet for said gas mixture such that said flame burns in said opening in said metal plate and an electrically conductive metal layer on said ceramic plate around said nozzle outlet in said ceramic plate. A negative pole of the DC voltage is connected to said metal plate as one of said electrodes, the positive pole of the DC voltage being connected to said metal layer as the other of said electrodes, and an output line is connected to said metal layer to provide an output signal.

BRIEF DESCRIPTION OF THE DRAWING

An embodiment of the flame ionization detector of the invention is shown in the sole FIGURE of the drawing which is a longitudinal, sectional view of the flame ionization chamber.

DETAILED DESCRIPTION

The drawing shows a flame ionization detector 1 having a pair of insulated electrodes 2, to which a d.c. voltage is applied. Between the electrodes a hydrogen flame 3 is burned, to which the gas to be measured, particularly an automobile exhaust gas, is introduced whereby the ions that are formed thereby produce a charge flow, which is measured as an ion current.

Flame ionization detector 1 is comprised of a base plate 4, which has channels 5 and 6 respectively for the inlet of combustion gas and the gas to be measured, which are joined in front of a central outlet connection 7, at which there is also connected a channel 8 for combustion air.

Outlet connection 7 is covered by a ceramic plate 9, which has a nozzle opening 10 for the outlet of the mixture of the combustion and exhaust gases and nozzle openings 11 for the discharge of the combustion air arranged around nozzle opening 10. A gasket 12 seals the gas nozzle opening 10 and the air nozzle openings 11 and the channels 7 and 8 from one another.

A metal plate 14 is arranged at a predetermined distance 13 above ceramic plate 9, and plate 13 has an opening 15 lying above nozzle opening 10, so that flame 3 burns in opening 15. Metal plate 14 is made from a special steel alloy or a light alloy metal and is electrically insulated from the rest of the construction.

The combustion gas nozzle opening 10 is surrounded by a signal electrode 16, which is present as a conductor path on the ceramic plate 9, and is connected to a measurement signal output line 17. Metal plate 14 serves as a negative electrode by being connected by line 18 to a negative pole of the d.c. voltage source.

The signal electrode 16 can be formed as a layer which is coated, vapor deposited, printed or attached as a punched-out conductor plate on ceramic plate 9.

It has proven advantageous to provide in the base plate 4 a second channel 19 for inlet of combustion gas and an inlet 20 for gas whose composition is to be measured. The gases are mixed and supplied to an outlet 21 communicating with a nozzle outlet 22 in the ceramic plate 9 to form a second flame 3'. The nozzle outlet 22 is surrounded by outlets 23 for combustion air. A separate signal electrode 24 is disposed on ceramic plate 9 in association with the second flame 3'. The metal plate 14 has a second opening 25 in which the second flame 3' burns. The signal electrode 24 is connected to a respective measurement signal output line 17'. In this way, measurement accuracy can be increased for the specific hydrocarbon compound in the exhaust gas. Alternatively, separate measurements can be conducted for different gases simultaneously.

If the same combustion gas to be measured is supplied to both inlets 6 and 20, the signal lines 17 and 17' can be connected together and provide a common output.

The flame ionization detector 1 has a cover 26, which is provided with an outlet 27 for discharging the combusted gases into the atmosphere, as well as a spark plug 28 for igniting the gases to produce flame 3 and/or 3' when detector 1 is placed in operation. For safety reasons, a flame sensor (not shown) can be provided for detecting whether the flame is burning. Flame ionization detector 1 can be opened by loosening cover screws 29 and metal plate 14 and ceramic plate 9 can be separated by loosening screws 30. All components are accessible from above.

Overall, a configuration that can be produced in a cost-favorable manner is provided by the flame ionization detector 1 according to the invention, which is appropriate for future need for exhaust pollutant reduction.

Although the invention is disclosed with reference to particular embodiments thereof, it will become apparent to those skilled in the art that numerous modifications and variations can be made which will fall within the scope and spirit of the invention as defined by the attached claims.

What is claimed:

1. A flame ionization detector comprising:
    a pair of spaced electrodes adapted for supply of a DC voltage thereto,
    means for producing a flame between the electrodes by burning a combustion gas and a gas whose composition is to be determined, said flame producing ions which form an ion current between said electrodes,
    said means comprising:
        a base plate having a first channel for inlet of the gas to be measured, a second channel for inlet for the combustion gas, a third channel connected to said first and second channels for conveying a mixture of the gases, an outlet for said third channel, a further channel for supply of combustion air thereto and further outlets for said combustion air, said further outlets surrounding the outlet of said third channel for the gas mixture,
        a ceramic plate on said base plate having a nozzle outlet communicating with said outlet of said third channel for discharging the mixture of the gases therefrom, and further nozzle outlets communicating with said further outlets of said further channel for discharging the combustion air therefrom,
        a metal plate spaced at a predetermined distance from said ceramic plate, said metal plate having an opening facing said nozzle outlet for said gas mixture such that said flame burns in said opening in said metal plate,
        an electrically conductive metal layer on said ceramic plate around said nozzle outlet in said ceramic plate to form a signal electrode,
        a negative pole of said DC voltage supply being connected to said metal plate as one of said pair of electrodes, a positive pole of said DC voltage supply being connected to said metal layer on said ceramic plate the other of said pair of electrodes, and
        a measurement signal output line connected to said metal layer.

2. A flame ionization detector as claimed in claim 1, wherein said base plate has a further inlet for a mixture of a gas to be measured and the combustion gas, a further outlet for said further inlet which is covered by said ceramic plate, said ceramic plate having a further nozzle outlet communicating with said further outlet in said base plate, said metal plate having a further opening facing said further nozzle outlet in said ceramic plate for formation of a second flame in said metal plate and a second separate signal electrode associated with said second flame and disposed on said ceramic plate around said further nozzle outlet therein.

3. A flame ionization detector as claimed in claim 1, wherein said electrically conductive metal layer is applied on said ceramic plate by coating, vapor-deposit, printing or as a distinct metal plate with said opening therein.

4. A flame ionization detector as claimed in claim 2, wherein said inlet and said further inlet are connected to the same source of gas to be measured and said first and second signal electrodes are connected together.

5. A flame ionization detector as claimed in claim 1, wherein said metal layer has openings for flow therethrough of combustion air coming from said base plate.

* * * * *